(12) United States Patent
Wattanasin et al.

(10) Patent No.: US 6,432,923 B1
(45) Date of Patent: Aug. 13, 2002

(54) VLA-4 ANTAGONISTS

(75) Inventors: Sompong Wattanasin, Hopatcong; Peter Josef Von Matt, Morristown, both of NJ (US)

(73) Assignee: Novartis AG, Basel (CH)

( * ) Notice: Subject to any disclaimer, the term of this patent is extended or adjusted under 35 U.S.C. 154(b) by 25 days.

(21) Appl. No.: 09/655,244

(22) Filed: Sep. 5, 2000

Related U.S. Application Data

(62) Division of application No. 09/233,517, filed on Jan. 19, 1999.
(60) Provisional application No. 60/113,653, filed on Jan. 23, 1998, and provisional application No. 60/110,723, filed on Dec. 3, 1998.
(51) Int. Cl.$^7$ ................................................ C07K 5/078
(52) U.S. Cl. ......................................... 514/19; 548/535
(58) Field of Search .............................. 514/19; 548/535

(56) References Cited

FOREIGN PATENT DOCUMENTS

| WO | WO 95/15973 | 6/1995 |
|---|---|---|
| WO | WO 96/22966 | 8/1996 |
| WO | WO 97/03094 | 1/1997 |
| WO | WO 98/04247 | 2/1998 |
| WO | WO 98/04913 | 2/1998 |

*Primary Examiner*—Christopher S. F. Low
(74) *Attorney, Agent, or Firm*—Norbert Gruenfeld

(57) ABSTRACT

Compounds of the formula I

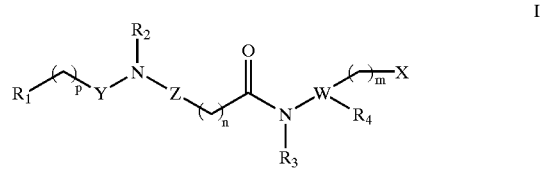

as defined, and their pharmaceutically acceptable salts are VLA-4 antagonists which are useful in inhibiting cell adhesion and in the therapeutic or prophylactic treatment of inflammatory and autoimmune diseases, particularly inflammatory airways diseases. They are particularly useful in reducing post-surgical inflammation, especially that resulting from transplant surgery.

4 Claims, No Drawings

VLA-4 ANTAGONISTS

CROSS REFERENCE TO RELATED APPLICATIONS

This application is a divisional application of application Ser. No. 09/233,517 filed Jan. 19, 1999, which in turn claims the benefit of both provisional application Ser. No. 60/113,653 (converted from application Ser. No. 09/012,336) filed Jan. 23, 1998, and provisional application No. 60/110,723, filed Dec. 3, 1998, all of which are incorporated herein by reference.

BACKGROUND OF THE INVENTION

Cell adhesion (i.e., a process by which cells associate with each other, migrate towards a specific target, or localize within the extracellular matrix) underlies many biological phenomena. Cell adhesion causes adhesion of hemoatopoietic to endothelial cells and the subsequent migration of those hemopoietic cells out of blood vessels and to the site of injury, thus playing a role in mammalian pathologies such as inflammation and immune reactions.

Various cell-surface macromolecules (known as cell adhesion receptors) mediate cell-cell and cell-matrix interactions. For example, the integrins are the key mediators in adhesive interactions between hematopoietic and other cells. Integrins are non-covalent heterodimeric complexes consisting of two subunits, α and β. Depending on the type of its α and β subunit components, each integrin molecule is categorized into its own subfamily. There are at least 12 different α subunits (α1-α6, α-L, α-M, α-X, α-IIB, α-V, and α-E) and at least 9 different β subunits (β1-β9).

The very late antigen-4 (VLA-4), also known as α4β1 integrin or CD49d/CD29, is a leukocyte cell surface receptor that participates in a variety of cell-cell and cell-matrix adhesions. It is a receptor for both the cytokine-inducible endorhelial cell surface protein, vascular cell adhesion molecule-1 (VCAM-1), and the extracellular matrix protein fibronectin (FN). Anti-VLA-4 monoclonal antibodies (mAb's) inhibit VLA-4-dependent adhesive interactions both in vitro and in vivo. This inhibition of VLA-4-dependent cell adhesion may prevent or inhibit several inflammatory and autoimmune pathologies.

WO 96/22966 describes compounds of the formula

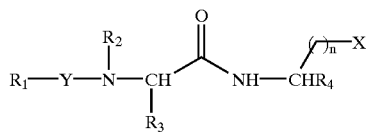

as useful for inhibition, prevention, and suppression of VLA-4-mediated cell adhesion.

SUMMARY OF THE INVENTION

This invention relates to organic compounds which are VLA-4 antagonists, the preparation of such compounds and their use as pharmaceuticals.

It has now been found that certain novel compounds have very good VLA-4 antagonistic activity and useful pharmacological properties.

DETAILED DESCRIPTION OF THE INVENTION

Accordingly, the present invention provides in one aspect compounds of formula I

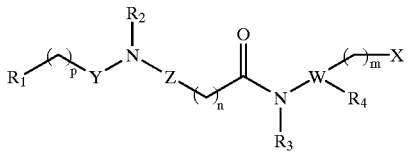

wherein $R_1$ is alkyl, alkenyl, alkynyl, cycloalkyl, aryl-fused cycloalkyl, cycloalkenyl, aryl, aryl-substituted alkyl (aralkyl), aryl-substituted alkenyl or alkynyl, cycloalkyl-substituted alkyl, cycloalkenyl-substituted cycloalkyl, biaryl, alkoxy, alkenoxy, alkynoxy, aryl-substituted alkoxy (aralkoxy), aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylureido-substituted alkyl, N-arylureido-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl, or heterocyclylalkyl;

$R_2$ is $(CH_2)_q$—V—$(CH_2)_q$—$V_r$—$R_S$;

$R_3$ is H, alkyl, alkenyl, aryl, or hereroaryl;

$R_4$ is H, aryl, alkyl, cycloalkyl, alkenyl, cycloalkenyl, alkynyl and aryl-substituted alkyl, heterocyclyl, heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, or alkyl optionally substituted by substituents selected from the group consisting of amino, halo, hydroxy, mercapto, mono- or dialkylamino, mono- or diarylamino, alkylarylamino, mono- or diacylamino, alkoxy, alkenoxy, aryloxy, thioalkoxy, thioalkenoxy, thioalkynoxy, thioaryloxy, and heterocyclyl;

$R_5$ is alkyl, alkenyl, alkynyl, cycloalkyl, cycloalkenyl, aryl, aryl-substituted alkyl, aryl-substituted alkenyl, or alkynyl; alkyl optionally substituted by substituents selected from the group consisting of amino, halo, hydroxy, mercapto, mono- or dialkylamino, mono- or diarylamino, alkylarylamino, mono- or diacylamino, alkoxy, alkenoxy, aryloxy, thioalkoxy, thioalkenoxy, thioalkynoxy, thioaryloxy, and heterocyclyl;

$R_6$ is alkyl, alkenyl, alkynyl, cycloalkyl, cycloalkenyl, aralkyl, aryl-substituted alkenyl or alkynyl, hydroxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, acylamino-substituted alkyl, alkylsulfonylamino-substituted alkyl, arylsulfonylamino-substituted alkyl, morpholino-alkyl, thiomorpholino-alkyl, morpholinocarbonyl-substituted alkyl, thiomorpholinocarbonyl-substituted alkyl, [N-(alkyl, alkenyl or alkynyl)- or (N,N-dialkyl, dialkenyl or dialkynyl)-amino]carbonyl-substituted alkyl, carboxyl-substituted alkyl, dialkylamino-substituted acylaminoalkyl; or amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryprophan, proline, alanine, ornithine, histidine, glutamine, valine, threonine, serine, asparric acid, beta-cyanoalanine, and allothreonine;

$R_7$ and $R_S$ are independently H, alkyl, alkenyl, carbocyclic aryl, heteroaryl, or alkyl, alkenyl, carbocyclic aryl or heteroaryl substituted by 1–3 substituents selected from the group consisting of amino, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy, and heterocyclyl;

or $R_2$ and $R_6$ taken together with the atoms to which they are attached may form a heterocycle;

V is O, NH, S, SO, or $SO_2$;

X is $CO_2R_5$, $PO_3H$, $SO_2R_5$, $SO_3H$, $OPO_3H$, $CO_2H$, or $CON(R_4)_2$;

W is CH or N;

Y is CO, $SO_2$, or $PO_2$;

Z is $(CH_2)_{n'}$, $CHR_6$, or $NR_7$;

n and n' are independently 0–4;

m is 1–4;

p is 1–4;

q and q' are independently 1–5; and r is 0 or 1;

or pharmaceutically acceptable salts thereof.

Compounds of the invention, i.e. compounds of formula I and their pharmaceutically acceptable salts, are VLA-4 antagonists and useful to prevent, suppress, or inhibit cell adhesions. Thus, they are useful in VLA-4-mediated cell adhesion disease states, particularly inflammation and autoimmune diseases. They are particularly useful in surgery-induced inflammation, especially transplant surgery. The compounds of the invention may be used alone or in combination with other agents active in the prevention, suppression, or inhibition of cell adhesion.

Another embodiment of the invention is a pharmaceutical composition, particularly a composition for VLA-4 antagonism, comprising an effective amount of a compound of the invention, optionally together with a pharmaceutically acceptable carrier.

In another aspect, the present invention also provides compounds of the invention, i.e. compounds of formula I or pharmaceutically acceptable salts thereof, for use as pharmaceuticals, particularly in VLA-4 antagonism.

In a further aspect the invention provides a method of antagonizing VLA-4 in a mammal which comprises administering to a mammal, preferably man, in need of such treatment an effective amount of a compound of the invention.

In a yet further aspect, the invention provides the use of a compound of the invention for the preparation of a medicament for the treatment of a disease mediated by VLA-4.

Particular embodiments of the invention relate to compounds of formula I or pharmaceutically acceptable salts thereof wherein (a) $R_1$ is aryl, particularly N-arylureido-substituted phenyl;

(b) $R_4$ is H, alkyl, alkenyl or aryl;

(c) W is CH;

(d) Y is CO;

(e) X is $CO_2H$ or $CO_2$alkyl;

(f) Z is $(CH_2)_{n'}$ or $CHR_6$.

Preferred compounds of the invention are those of formula Ia

Ia wherein $R_2$ is $C_{1-4}$alkyl-oxy-$C_{1-8}$alkyl;

$R_4$ is H, alkyl, alkenyl, carbocyclic aryl or heteroaryl;

X is $CO_2H$ or $CO_2$alkyl;

and the other symbols are as defined for formula I; or pharmaceutically acceptable salts thereof.

More-preferred compounds of the invention are those of formula Ia wherein $R_1$ is aryl; $R_2$ is methoxy-n-propyl; $R_3$ is H; $R_4$ is alkenyl or aryl; X is $CO_2H$; n is 0; and W is CH; or pharmaceutically acceptable salts thereof.

A particular embodiment of the invention is directed to compounds of formula Ib

Ib wherein $R_1$ is N-arylureidophenyl;

$R_2$ is $C_1$–$C_4$-alkyl-oxy-$C_2$–$C_4$-alkyl;

$R_3$ is H;

$R_4$ is H, $C_1$–$C_4$-alkyl, $C_2$–$C_4$-alkenyl or carbocyclic aryl;

n is 1 or 2;

m is 1, 2 or 3;

X is COOH or $CO_2R_5$; and $R_5$ is optionally substituted lower alkyl;

or pharmaceutically acceptable salts thereof.

Preferred are the compounds of formula Ib wherein $R_1$ is N-(optionally substituted phenyl)-ureidophenyl;

$R_2$ is methoxypropyl;

$R_3$ is H;

$R_4$ is $C_2$–$C_4$-alkenyl or optionally substituted phenyl;

n is 1;

m is 1; and

X is COOH;

or pharmaceutically acceptable salts thereof.

Another particular embodiment of the invention is directed to compounds of formula Ic

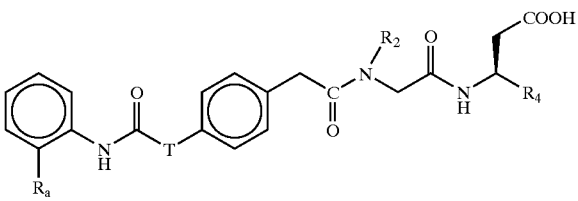

Ic wherein

R$_a$ is H, CH$_3$, Cl or NH$_2$;

R$_2$ is (CH$_2$)$_3$OCH$_3$ or (CH$_2$)$_4$OCH$_3$;

R$_4$ is —(CH)═(CH)—CH$_3$, phenyl, 4-methoxyphenyl, or 3,4-dimethoxyphenyl; and T is NH or CH$_2$;

or pharmaceutically acceptable salts thereof.

Most-preferred compounds of the invention are those of formula Id

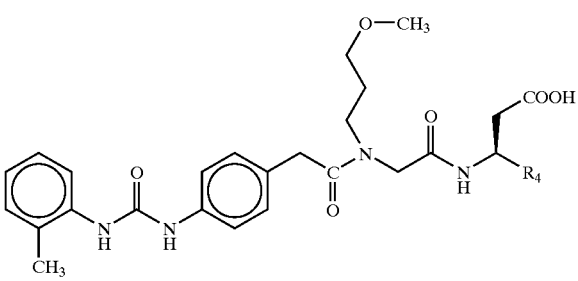

Id wherein

R$_4$ is —(CH)═(CH)—CH$_3$, phenyl, 4-methoxyphenyl, or 3,4-dimethoxyphenyl;

or the pharmaceutically acceptable salts thereof.

"Alkyl" means a straight-chain or branched-chain alkyl radical containing from 1 to 10, preferably from 1 to 6, and more preferably from 1 to 4, carbon atoms. Examples of such radicals include methyl, ethyl, n-propyl, isopropyl, n-butyl, isobutyl, sec-butyl, tert-butyl, pentyl, iso-amyl, hexyl, and decyl.

"Alkenyl" means a straight-chain or branched-chain alkenyl radical containing from 2 to 10, preferably from 2 to 6, and more preferably from 2 to 4, carbon atoms. Examples of such radicals include etheryl, E- and Z-propenyl, isopropenyl, E- and Z-butenyl, E- and Z-isobutenyl, E- and Z-pentenyl, and decenyl.

"Lower" in conjunction with the above terms means a said radical containing up to 6 carbon atoms. "Substituted" in conjunction with the above terms means a said radical substituted by e.g. amino, halo, hydroxy, mercapto, mono- or dialkylamino, mono- or di-arylalkylamino, mono- or diarylamino, alkoxy, aryloxy, aryl, thioaryloxy, thioalkoxy or heterocyclyl.

"Alkynyl" means a straight-chain or branched-chain alkynyl radical containing from 2 to 10, preferably from 2 to 6, and more preferably from 2 to 4, carbon atoms. Examples of such radicals include ethynyl (acetylenyl), propynyl, propargyl, butynyl, hexynyl, and decynyl.

"Cycloalkyl" means a cyclic alkyl radical containing from 3 to 8, preferably from 3 to 6, carbon atoms. Examples of such cycloalkyl radicals include, cyclopropyl, cyclobutyl, cyclopentyl, cyclohexyl, and cyclopropyl methyl.

"Cycloalkenyl" means a cyclic carbocycle containing from 4 to 8, preferably 5 to 6, carbon atoms and one or more double bonds. Examples of such cycloalkenyl radicals include cyclopentenyl, cyclohexenyl, cyclopentadienyl, and 2-methyl-2-butenyl.

Aryl means carbocyclic or heterocyclic aryl (heteroaryl).

"Aryl" (carbocyclic aryl and heteroaryl) means a 5- or 6-membered carbocyclic aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or a tricyclic 13- or 14-membered aromatic or heteroaromatic ring system containing 0–3 heteroatoms selected from O, N, and S; each of which rings is optionally substituted with 1–3 substituents selected from e.g. lower alkyl, alkenyl, alkynyl, substituted lower alkyl, substituted alkenyl, substituted alkynyl, ═O, NO$_2$, halogen, hydroxy, alkoxy, cyano, —NR'R', acylamino, phenyl, benzyl, phenoxy, benzyloxy, hereroaryl, and heteroaryloxy, wherein each of said phenyl, benzyl, phenoxy, benzyloxy, heteroaryl, and heteroaryloxy is optionally substituted with 1–3 substituents selected from e.g. lower alkyl, alkenyl, alkynyl, halogen, hydroxy, alkoxy, cyano, phenyl, phenoxy, benzyl, benzyloxy, carboxy, carboalkoxy, carboxamido, heteroaryl, heteroaryloxy, NO$_2$, and —NR'R', wherein R' is H or lower alkyl. The carbocyclic aromatic ring systems comprise phenyl, naphthyl, indenyl, indanyl, azulenyl, fluorenyl, anthracenyl. The heterocyclic aromatic ring systems comprise furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl", as it relates in particular to the grouping R$_1$ in the above formulae, means carbocyclic or heterocyclic aryl, particularly phenyl optionally substituted by one to three substituents which are independently selected from e.g. halo, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl such as alkanoyl, Ar'-substituted alkanoyl or Ar'-substituted carbonyl, Ar'-substituted alkylcarbonyloxy, Ar'-substituted carbonylamino, substituted amino, Ar'-substituted oxy, alkylcarbonylamino, Ar'-substituted alkylcarbonylamino, Ar'-substituted aminocarbonylalkyl, alkoxy-carbonylamino, Ar'-substituted alkoxycarbonyl-amino, Ar'-oxycarbonylamino, alkylsulfonylamino, mono- or bis-(Ar'-sulfonyl) amino, Ar'-substituted alkyl-sulfonylamino, morpholinocarbonylamino, thiomorpholinocarbonylamino, N-alkyl guanidino, N-Ar' guanidino, N-Ar' cyano-guanidino, N-N-(Ar'-, alkyl) guanidino, N,N-(Ar', Ar') guanidino, N,N-dialkyl guanidino, N,N,N-trialkyl guanidino, N-alkyl-ureido, N,N-dialkyl-ureido, N-Ar'-ureido, N,N-(Ar',alkyl) ureido and N,N-(Ar')$_2$ ureido; acylcarbonylamino; Ar'-substituted aryl; aromatic acyl-substicuted aromatic or aliphatic acyl; Ar'-substituted heterocyclyl; Ar'-substituted cycloalkyl or cycloalkenyl; heterocyclylalkoxy; N,N-(Ar', hydroxyl)ureido; Ar'-substituted cycloalkyl and cycloalkenyl; Ar'-substituted biaryl; Ar'-substituted aminocarbonylamino; Ar'-mercapto-substituted alkyl; Ar'-amino-substituted aryl; Ar'-oxy-substituted alkyl; Ar'-substituted aminocycloalkyl and cycloalkenyl; aralkylaminosulfonyl; aralkoxyalkyl; N-Ar'-substituted thioureido; N-aralkoxyureido; N-hydroxylureido; N-alkenylureido; N,N-(alkyl,hydroxyl)ureido; heterocyclyl; thioaryloxy-substituted aryl; N,N-(aryl,alkyl)hydrazino; Ar'-substituted sulfonylheterocyclyl; aralkyl-substituted heterocyclyl; cycloalkyl and cycloalkenyl-substituted heterocyclyl; cycloalkyl-fused aryl; aryloxy-substituted alkyl; heterocyclylamino; Ar'-substituted arylaminosulfonyl; Ar'-substituted alkenoyl; aliphatic or aromatic acylaminocarbonyl; aliphatic or aromatic acyl-substituted alkenyl; Ar'-substituted aminocarbonyloxy; Ar',Ar'-disubstituted aryl; aliphatic or aromatic acyl-substituted acyl; benzofused-heterocyclylcarbonylamino; Ar'-subsrituted hydrazino; Ar'-substituted aminosulfonyl; Ar'-substituted alkylamino; Ar'-substituted heterocyclyl; Ar',Ar'-disubstituted alkanoylamino; Ar'-substituted cycloalkanoylamino; hererocyclylalkoxy; N,N-Ar',hydroxylureido; N,N'-Ar', hydroxylureido; heterocyclylcarbonylamino; Ar'-substituted aminocarbonylheterocyclyl; Ar'-substituted aminocarbonyl, Ar'-substituted carbonylamino; Ar'-substituted aminosulfonylamino; Ar'-substituted mercaptoalkyl; Ar'-amino substituted biaryl; aralkylaminoalkoxy; alkyl- and aryloxy-substituted alkoxy; hererocyclylcarbonyl; Ar'-substituted sulfonylalkyl; Ar'-amino carbocyclyl; aralkylsulfonyl; aryl-substituted alkenyl; heterocyclylalkylamino; heterocyclylalkylaminocarbonyl; Ar'-substituted sulfonylaminoalkyl; Ar'-substituted cycloalkyl; thioaryloxyalkyl; thioaryloxymercapto; cycloalkylcarbonylalkyl; cycloalkyl-substituted amino; Ar'-substituted arylamino; aryloxycarbonylalkyl; phosphorodiamidyl acid or ester; aryloxydimethylsiloxy; 1,3-indandionylcarbonylalkyl; 1,3-indandionylcarbonyl; oxamidyl; heterocyclylalkylidenyl; formamidinyl; benzalizinyl; benzalhydrazino; arylsulfonylureido; benzilylamino; 4-(N-2-carboxyalkyl-1-(1,3-benzodioxol-5-yl)-amino-N-leucinylalkylamidylarylurea); Ar'-carbamoyloxy and alkyl- and aryloxy-substituted ureido; wherein "Ar'" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkylureido.

"Alkoxy" means an alkyl ether radical. Examples of alkyl ether radicals include methoxy, ethoxy, n-propoxy, iso-propoxy, n-butoxy, iso-butoxy, sec-butoxy, and tert-butoxy. "Alkenoxy" means a radical of formula alkenyl-O-, provided that the radical is not an enol ether. Examples of alkenoxy radicals include allyloxy and E- and Z-3-methyl-2-propenoxy. "Alkynyloxy" means a radical of formula alkynyl-O-, provided that the radical is not an ynol ether. Examples of alkynoxy radicals include propargyloxy and 2-butynyloxy. "Thioalkoxy" means a thioether radical of formula alkyl-S-. "Alkylamino" means a mono- or di-alkyl-substituted amino radical (i.e., a radical of formula alkyl-NH- or (alkyl)$_2$-N-). Examples of alkylamino radicals include methylamino, ethylamino, propylamino, isopropylamino, t-butylamino, and N,N-diethylamino. "Alkenylamino" means a radical of formula alkenyl-NH- or (alkenyl)$_2$N-, provided that the radical is not an enamine. An example of an alkenylamino radical is the allylamino radical. "Alkynylamino" means a radical of formula alkynyl-NH— or (alkynyl)$_2$N—, provided that the radical is not an ynamine. An example of an alkynylamino radical is the propargyl amino radical. "Aryloxy" means a radical of formula aryl-O—. Examples of aryloxy radicals include phenoxy, naphthoxy, and pyridyloxy. "Arylamino" means a radical of formula aryl-NH—. Examples of arylamino radicals include phenylamino (anilido), naphthylamino, 2-, 3- or 4-pyridylamino. "Biaryl" means a radical of formula aryl-aryl-. "Thioaryl" means a radical of formula aryl-S—. An example of a thioaryl radical is the thiophenyl radical. "Aryl-fused cycloalkyl" means a cycloalkyl radical which shares two adjacent atoms with an aryl radical. An example of an aryl-fused cycloalkyl radical is the benzofused cyclobutyl radical. "Aliphatic acyl" means a radical of the formula alkyl-CO—, alkenyl-CO—, or alkynyl-CO— derived from a carboxylic acid. Examples of aliphatic acyl radicals include acetyl, propionyl, butyryl, valeryl, 4-methylvaleryl, acryloyl, crotyl, propiolyl, and methylpropiolyl. "Aromatic acyl" means a radical of the formula aryl-CO—. Examples of aromatic acyl radicals include benzoyl, 4-halobenzoyl, 4-carboxybenzoyl, naphthoyl, and pyridylcarbonyl. "morpholinocarbonyl" and "thiomorpholinocarbonyl" mean an N-carbonylated morpholino and an N-carbonylated thiomorpholino radical, respectively. "Alkylcarbonylamino" means a radical of formula alkyl-CONH—. "Alkoxycarbonylamino" means a radical of formula alkyl-OCONH—. "Alkylsulfonylamino" means a radical of formula alkyl-SO$_2$NH—. "Arylsulfonylamino" means a radical of formula aryl-SO$_2$NH—. "N-alkylurea" or "N-alkylureido" means a radical of formula alkyl-NH—CO—NH—. "N-arylurea" or "N-arylureido" means a radical of formula aryl-NH—CO—NH—. "Halogen" or "halo" means fluoro, chloro, bromo, and iodo. "Heterocycle", unless otherwise defined herein, means a stable 3–7 membered monocyclic heterocyclic ring or an 8–11 membered bicyclic heterocyclic ring which is saturated or unsaturated, and which may be optionally benzofused. Each heterocycle consists of one or more carbon atoms and from one to four heteroatoms selected from nitrogen, oxygen, and sulfur, any oxidized form of nitrogen and sulfur, and the quaternized form of any basic nitrogen. Any ring nitrogen may be optionally substituted with a substituent $R^4$, as defined herein for compounds of formula I. A heterocycle may be attached at any endocyclic carbon or heteroatom which results in the creation of a stable structure. Preferred heterocycles include 5–7 membered monocyclic heterocycles and 8–10 membered bicyclic heterocycles. Heterocycles may be optionally oxo-substituted at 1–3 ring positions and may optionally be independently substituted with 1–4 aryl substituents. Included are heteroaryl groups as defined herein and saturated heterocycles such as piperidine, morpholine, pyrrolidine, thiazolidine, piperazine and the like.

It is intended that the definitions of any substituent or symbol in a particular molecule be independent of irs definitions elsewhere in the molecule. Thus, for example, —N(R$_4$)$_2$ represents —NH$_2$, —NHCH$_3$, —N(CH$_3$)$_2$ etc.

Some of the compounds described herein contain one or more asymmetric centers and may thus give rise to enantiomers, diastereomers, and other stereoisomeric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D) and (L), isomers may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

In a preferred group of compounds of the invention, where W in formula I is CH, the stereochemistry at this carbon atom is (S), i.e. the compounds are of formula Ie

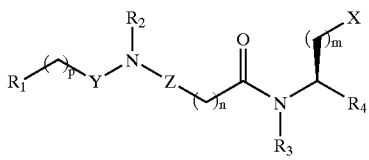

where $R_1$, $R_2$, $R_3$, $R_4$, X, Y, Z, m, n and p are as defined for formula I, and their pharmaceutically acceptable salts.

The pharmaceutical compositions of the present invention comprise a compound of Formula I or a pharmaceutically acceptable salt thereof as an active ingredient, and may also contain a pharmaceutically acceptable carrier and, optionally, other therapeutic ingredients. The term "pharmaceutically acceptable salts" refers to salts prepared from pharmaceutically acceptable non-toxic acids or bases including organic and inorganic acids or bases.

When a compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N'-dibenzylethylenediamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, isopropylamine, lysine, methylglucosamine, morpholine, piperazine, piperidine, polyamine resins, procaine, purine, theobromine, triethylamine, trimethylamine, tripropylamine, etc.

When a compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tarraric acids. Base salts also include ammonium, alkali metal, and alkaline earth metal salts, salts with organic bases, such as dicyclohexylamine salts, and salts with amino acids such as arginine and lysine. Also, basic nitrigen-containing groups can be quaternized with such agents as lower alkyl halides, such as methyl chloride, dialkyl sulfates, such as dimethyl, sulfates, long chain halides such as stearyl chlorides, and aralkyl halides, such as benzyl chlorides.

The compounds of the invention are particularly useful in mammals as VLA-4 antagonists and as inhibitors of VLA-4 associated cell adhesion.

The ability of the compounds of formula I to inhibit VLA-4-associated cell adhesions makes them useful for treating, ameliorating, or preventing a variety of inflammatory, immune and autoimmune diseases. Preferably the diseases to be treated with the methods of this invention are selected from respiratory disorders (such as asthma), arthritis, psoriasis, transplantation rejection, multiple sclerosis, type I diabetes, and inflammatory bowel disease, stem cell mobilization and engraphment, and sickle cell anemia. The compounds of formula I are also useful in transplantation surgery; specifically, for the treatment of xenograft and allograft rejection, both chronic and acute.

As to the respiratory diseases, the compounds of the invention are useful as agents for the symptomatic or prophylactic treatment of inflammatory airways diseases. Such diseases include asthma of whatever type or genesis including both intrinsic (non-allergic) asthma and, especially, extrinsic (allergic) asthma. They are useful for the treatment of bronchitic asthma, exercise-induced asthma, occupational asthma, asthma induced following bacterial infection and other non-allergic asthmas. Treatment of asthma is also to be understood as embracing treatment of patients of less than 4 or 5 years of age exhibiting wheezing symptoms, particularly at night and diagnosed or diagnosable as "wheezy infants".

Prophylactic efficacy in the treatment of asthma may be manifested by reduced frequency or reduced severity of symptomatic attack, improvement in lung function or improved airways hypereactivity. It may be further evidenced by reduced requirement for symptomatic therapy, i.e. therapy for, or intended to restrict or abort, symptomatic attack when it occurs, for example for anti-inflammatory therapy using a corticosteroid.

Other inflammatory airways diseases which may be treated with compounds of the invention include pneumoconiosis (an inflammatory, commonly occupational, disease of the lungs occasioned by repeated inhalation of dusts) including for example aluminosis, asbestosis, chalicosis, siderosis, silicosis, tabacosis and byssinosis.

Further inflammatory airways diseases which may be treated with compounds of the invention include adult respiratory distress syndrome (ARDS), chronic obstructive pulmonary disease (COPD) in the exacerbation phase thereof and exacerbation of airways hyperactivity consequent to other drug therapy, e.g. aspirin or b-agonist bronchodilator therapy.

In view of their anti-inflammatory activity, particularly in relation to inhibition of eosinophil activation, compounds of the invention are also useful for the treatment of related disorders of the airways, e.g. eosinophilia, hypereosinophilia, eosinophilic pneumonia, parasitic infestation (including tropical eosinophilia), bronchopulmonary aspergillosis, polyarteritis nodosa, eosinophilic granuloma and eosinophil-related disorders affecting the airways caused by drug-reaction.

Compounds of the invention may also be used in the treatment of allergic inflammatory diseases such as allergic rhinitis.

In accordance with the foregoing, the invention includes:
(A) the use of a compound of the invention, i.e. a compound of formula I or a pharmaceutically acceptable salt thereof, as hereinbefore described, for the preparation of a medicament for the treatment of inflammatory, immune or autoimmune diseases, particularly arthritis, transplant rejection or inflammatory airways diseases, especially asthma; and
(B) a method of treating an inflammatory, immune or autoimmune disease, particularly arthritis, transplant rejection or an inflammatory airways disease, especially asthma, which comprises administering to a mammal, particularly a human, in need of such treatment a compound of the invention as hereinbefore described.

The dosage in vitro may range between about $10^{-6}$ and $10^{-10}$ molar concentrations, preferably between about $10^{-7}$ and $10^{-9}$ molar concentrations.

The magnitude of the prophylactic or therapeutic dose of the compounds of the invention will vary with the nature and severity of the condition to be treated with the mammal involved and with the particular compound of the invention and its route of administration. In general, the daily dose range lies in the range of 200 to 0.001 mg/kg body weight of a mammal, preferably 50 to 0.05 mg/kg, and most preferably 1.0 to 0.1 mg/kg, in single or divided doses. In some cases, it may be necessary to use doses outside these ranges. When a composition for intravenous administration is employed, a suitable daily dosage range is from about 50 to 0.0005 mg (preferably 20 to 0.01 mg) compound of the invention per kg body weight. When a composition for oral administration is employed, a suitable daily dosage range is from about 20 to 0.001 mg (preferably 10 to 0.01 mg) compound of the invention per kg body weight. When a composition for ophthalmic administration is employed, a suitable daily dosage range is from about 10–0.01% (preferably 5.0–0.5% compound of the invention, typically prepared as a 2.0–0.1% by weight solution or suspension of the compound in an acceptable ophthalmic formulation.

The compounds of the invention may also be used in combination with other pharmaceutically active ingredients. For example, a typical ocular formulation may comprise the compound alone or in combination with a b-adrenergic blocking agent such as timolol maleate or a parasympachomimetic agent such as pilocarpine. When used in combination, the two active ingredients are present in approximately equal parts.

Any suitable route of administration may be employed for providing a mammal, especially a human, with an effective dosage of a compound of the invention. For example, oral, rectal, topical, parenteral, ocular, pulmonary, nasal, etc. routes may be employed. Dosage forms include tablets, troches, dispersions, suspensions, solutions, capsules, creams, ointments, aerosols, and the like.

The pharmaceutical compositions of the present invention comprise a compound of Formula I, or a pharmaceutically acceptable salt thereof, as an active ingredient, and may also contain a pharmaceutically acceptable carrier and, optionally, other therapeutically active ingredients. The invention includes such compositions for use in the treatment of an inflammatory, immune or autoimmune disease, particularly arthritis, transplant rejection or an inflammatory airways disease, especially asthma.

The compositions include compositions suitable for oral, rectal, topical (including transdermal devices, aerosols, creams, ointments, lotions, and dusting powders), parenteral (including subcutaneous, intramuscular, and intravenous), ocular (ophthalmic), pulmonary (nasal or buccal inhalation), or nasal administration; although the most suitable route in any given case will depend largely on the nature and severity of the condition being treated and on the nature of the active ingredient. They may be conveniently presented in unit dosage form and prepared by any of the methods well known in the art of pharmacy.

For example, in the treatment of airways diseases, compounds of the invention may be administered orally, for example in tablet form, or by inhalation, for example in aerosol or other atomisable formulations or in dry powder formulations, using an appropriate inhalation device such as those known in the art. For use in the treatment of allergic rhinitis, the compounds of the invention may also be administered intranasally.

A compound of the invention may be combined as the active ingredient in intimate admixture with a pharmaceutical carrier according to conventional pharmaceutical compounding techniques. The carrier may take a wide variety of forms depending on the nature of the preparation desired for administration, i.e., oral, parenteral, etc. In preparing oral dosage forms, any of the usual pharmaceutical media may be used, such as water, glycols, oils, alcohols, flavoring agents, reservatives, coloring agents, and the like in the case of oral liquid preparations (e.g., suspensions, elixirs, and solutions); or carriers such as starches, sugars, microcrystalline cellulose, diluents, granulating agents, lubricants, binders, disintegrating agents, etc. in the case of oral solid preparations such as powders, capsules, and tablets. Solid oral preparations are preferred over liquid oral preparations. Because of their ease of administration, tablets and capsules are the preferred oral dosage unit form. If desired, capsules may be coated by standard aqueous or non-aqueous techniques.

In addition to the dosage forms described above, the compounds of the invention may be administered by controlled release means and devices.

Pharmaceutical compositions of the present invention suitable for oral administration may be prepared as discrete units such as capsules, cachets, or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, the compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent, or surface active or dispersing agent. Molded tablets may be made by molding in a suitable machine, a mixture of the powdered compound moistened with an inert liquid diluent. Ophthalmic inserts are made from compression molded films which are prepared on a Carver Press by subjecting the powdered mixture of active ingredient and HPC to a compression force of 12,000 lb. (gauge) at 149° C. for 1–4 min. The film is cooled under pressure by having cold water circulate in the platen. The inserts are then individually cut from the film with a rod-shaped punch. Each insert is placed in a vial, which is then placed in a humidity cabinet (88% relative humidity at 30° C.) for 2–4 days. After removal from the cabinet, the vials are capped and then autoclaved at 121° C. for 0.5 hr.

The compositions containing a compound of this invention may also comprise an additional agent selected from the group consisting of cortiocosteroids, bronchodilators, anti-asthmatics (mast cell stabilizers), anti-inflammatories, antirheumatics, immunosuppressants, antimetabolites, immunonodulators, antipsoriatics, and antidiabetics. Specific compounds include theophylline, sulfasalazine and aminosalicylates (anti-inflammatories); cyclosporin, FK-506, and rapamycin (immunosuppressants); cyclophosphamide and methotrexate (antimetabolites); and interferons (immunomodulators).

The invention includes a compound of the invention as hereinbefore described in inhalable form and an inhalable medicament comprising such a compound in inhalable form optionally together with a pharmaceutically acceptable carrier in inhalable form.

The inhalable form may be, for example, an atomisable composition such as an aerosol comprising the compound of the invention in solution or dispersion in a propellant or a nebulizable composition comprising a dispersion of the compound of the invention in an aqueous, organic or aqueous/organic medium, or a finely divided particulate form comprising the compound of the invention in finely divided form optionally together with a pharmaceutically acceptable carrier in finely divided form.

An aerosol composition suitable for use as the inhalable form may comprise the compound of the invention in solution or dispersion in a propellant, which may be chosen from any of the propellants known in the art. Suitable such propellants include hydrocarbons such as n-propane, n-butane or isobutane or mixtures of two or more such hydrocarbons, and halogen-substituted hydrocarbons, for example fluorine-substituted methanes, ethanes, propanes, butanes, cyclopropanes or cyclobutanes, particularly 1,1,1, 2-tetrafluoroethane (HFA134a) and heptafluoropropane (HFA227), or mixtures of two or more such halogen-substituted hydrocarbons. Where the compound of the invention is present in dispersion in the propellant, i.e. where it is present in particulate form dispersed in the propellant, the aerosol composition may also contain a lubricant and a surfactant, which may be chosen from those lubricants and surfactants known in the art. The aerosol composition may contain up to about 5% by weight, for example 0.002 to 5%, 0.01 to 3%, 0.015 to 2%, 0.1 to 2%, 0.5 to 2% or 0.5 to 1%, by weight of the compound of the invention, based on the weight of the propellant. Where present, the lubricant and surfactant may be in an amount up to 5% and 0.5% respectively by weight of the aerosol composition. The aerosol composition may also contain ethanol as co-solvent in an amount up to 30% by weight of the composition, particularly for administration from a pressurised metered dose inhalation device.

A finely divided particulate form, i.e. a dry powder, suitable for use as the inhalable form may comprise the compound of the invention in finely divided particulate form, optionally together with a finely divided particulate carrier, which may be chosen from materials known as carriers in dry powder inhalation compositions, for example saccharides, including monosaccharides, disaccharides and polysaccharides such as arabinose, glucose, fructose, ribose, mannose, sucrose, lactose, maltose, starches or dextran. As especially preferred carrier is lactose. The dry powder may be in capsules of gelatin or plastic, or in blisters, for use in a dry powder inhalation device, preferably in dosage units of 5 pg to 40 mg of the active ingredient. Alternatively, the dry powder may be contained as a reservoir in a multi-dose dry powder inhalation device.

In the finely divided particulate form, and in the aerosol composition where the compound of the invention is present in particulate form, the compound of the invention may have an average particle diameter of up to about 10 $\mu$m, for example 1 to 5 $\mu$m. The particle size of the compound of the invention, and that of a solid carrier where present in dry powder compositions, can be reduced to the desired level by conventional methods, for example by grinding in an air-jet mill, ball mill or vibrator mill, microprecipitation, spray-drying, lyophilisation or recrystallisation from supercritical media.

The inhalable medicament may be administered using an inhalation device suitable for the inhalable form, such devices being well known in the art. Accordingly, the invention also provides a pharmaceutical product comprising a compound of the invention in inhalable form as hereinbefore described in association with an inhalation device. In a further aspect, the invention provides an inhalation device containing a compound of the invention in inhalable form as hereinbefore described.

Where the inhalable form is an aerosol composition, the inhalation device may be an aerosol vial provided with a valve adapted to deliver a metered dose, such as 10 to 100 $\mu$l, e.g. 25 to 50 $\mu$l, of the composition, i.e. a device known as a metered dose inhaler. Suitable such aerosol vials and procedures for containing within them aerosol compositions under pressure are well known to those skilled in the art of inhalation therapy. Where the inhalable form is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer such as an AERx (ex Aradigm, US) or BINEB (Boehringer Ingelheim) nebulizer which allows much smaller nebulized volumes, e.g. 10 to 100 $\mu$l, than conventional nebulizers. Where the inhalable form is the finely divided particulate form, the inhalation device may be, for example, a dry powder inhalation device adapted to deliver dry powder from a capsule or blister containing a dosage unit of the dry powder or a multidose dry powder inhalation device adapted to deliver, for example, 25 mg of dry powder per actuation. Suitable such dry powder inhalation devices are well known.

The activities and VLA-4 specificities of the compounds of this invention may be determined using in vitro and in vivo assays.

The cell adhesion inhibitory activity of these compounds may be measured by determining the concentration of inhibitor required to block the binding of VLA-4-expressing cells to fibronectin-, CS1- or VCAM-I-coated plates. In this assay microtiter wells are coated with either fibronectin (containing the CS-1 sequence) or CS-1 or VCAM-I. If CS-1 is used, it must be conjugated to a carrier protein, such as bovine serum albumin, in order to bind to the wells. Once the wells are coated, varying concentrations of the test compound are then added together with appropriately labeled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound. VLA-4-expressing cells that may be utilized in this assay include Ramos cells, Jurkat cells, A375 melanoma cells, as well as human peripheral blood lymophocytes (PBLs). The cells used in this assay may be fluorescently or radioactively labeled.

A direct binding assay may also be employed to quantitate the inhibitory activity of the compounds of this invention. In this assay, a VCAM-IgG fusion protein containing the first two immunoglobin domains of VCAM (D1D2) attached above the hinge region of an IgGI molecule (VCAM 2D-IgG), is conjugated to a marker enzyme, such as alkaline phosphatase (AP). The synthesis of this VCAM-IgG fusion is described in PCT publication WO 90/13300. The conjugation of that fusion to a marker enzyme is achieved by well known crosslinking methods. The VCAM-IgG enzyme conjugate is then placed in the wells of a multi-well filtration plate, such as that contained in the Millipore Multiscreen Assay System (Millipore Corp., Bedford, Mass.). Varying concentrations of the test inhibitory compound are then added to the wells followed by addition of VLA-4-expressing cells. The cells, compound and VCAM-IgG enzyme conjugate are mixed together and allowed to incubate at room temperature. Following incubation, the wells are vacuum drained, leaving behind the cells and any bound VCAM. Quantitation of bound VCAM is determined by adding an appropriate colorimetric substrate for the enzyme conjugated to VCAM-IgG and determining the amount of reaction cell adhesion inhibitory activity.

Compounds of the Examples have measured IC50 values for VLA-4 binding of an order as low as 1 nanomolar.

In order to assess the VLA-4 inhibitory specificity of the compounds of this invention, assays for other major groups of integrins, i.e., β2 and β3, as well as other β1 integrins, such as VLA-5, VLA-6 and α4β7 are performed. These assays may be similar to the adhesion inhibition and direct binding assays described above, substituting the appropriate integrin-expressing cell and corresponding ligand. For example, polymorphonuclear cells (PMNs) express β2 integrins on their surface and bind to ICAM. β3 integrins are involved in platelet aggregation and inhibition may be measured in a standard platelet aggregation assay. VLA-5 binds specifically to Arg-Gly-Asp sequences, while VLA-6 binds to laminin. Compounds of the Examples are found to be selective for VLA-4 versus related integrins.

An in vivo assay which tests the inhibition of contact hypersensitivity in an animal is described in P. L. Chisholm et al., Eur. J. Immunol., vol. 23, pp. 682–688 (1993).

An assay which measures the inhibition of Ascaris antigen-induced late phase airway responses and airway hyperresponsiveness in asthmatic sheep is described in W. M. Abraham et al., J. Clin. Invest., vol. 93, pp. 776–87 (1994).

The compounds of the invention may also be tested in the following assay.

Antigen-induced Pulmonary Eosinophilia in the Mouse

Sensitization of mice: Male B6D2F1/J mice are sensitized by i.p. injection of 0.5 mL alum-precipitated antigen containing 8 μg of ovalbumin (OVA) adsorbed to 2 mg of aluminum hydroxide gel in a saline vehicle. Five days later the mice are given a booster injection with OVA/alum. Control animals are sensitized with alum only. Ten mice are used for each group.

Challenge and drug administration: Mice are placed in a 12×14×10 inch plexiglass chamber and exposed to aerosolized OVA (0.5% in saline) for 1 hour at the beginning of the experiment (t=0), and five hours later. Low molecular weight antagonists are dissolved in 2% DMSO and 150 mM TRIS, pH 8.8. A solvent control is included for each experiment. Drugs are administered orally 30 min prior to OVA exposure, and 6 hour after the first OVA exposure. BAL fluid collection and analysis: Animals are sacrificed by $CO_2$ asphyxiation 24 hour after the first antigen challenge. The tracheas are exposed and cannulated. The lungs are lavaged with 0.6 mL buffer (Hanks buffered saline with 10 mM Hepes, 0.5% BSA and 10 U/mL heparin). The number of eosinophils in the lavage is assessed by counting the total number of leukocytes and the percentage of eosinophils for each sample.

The % inhibition is calculated by the formula:

$$1 - \frac{(\# \text{ Eos with drug in OA goup} - \# \text{ Eos in no OA group})}{(\# \text{ Eos in OA group} - \# \text{ Eos in no OA group})} \times 100\%$$

where:

Eos=average number of eosinophils, OA=challenged and no OA=unchallenged mice.

In this assay, compounds of the Examples administered at a dosage of 30 mg/kg give percentage inhibition of eosinophilia values up to 77%.

The compounds of the invention may be synthesized using known techniques. See, e.g., WO 96/22966, incorporated herein by reference, which teaches the synthesis of analogous compounds. The invention is further defined by reference to the following examples, which are intended to be illustrative and not limiting. For example, representative compounds of formula I wherein W is CH are prepared by reacting a compound of formula II

wherein $R_1$, p and Y have meaning as defined hereinabove, or a reactive functional derivative thereof, with a compound of the formula III

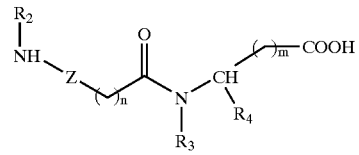

wherein the carboxyl group is in protected form and wherein $R_2$–$R_4$, Z, n and m have meaning as defined hereinabove, and if desired, converting a compound so obtained to another compound of the invention. The condensation is carried out according to methodology well known in the art for amide formation, e.g. in the presence of a condensing agent such as 1-[3-(dimethylamino)propyl]-3-ethylcarbodiimide hydrochloride and a base, such as diisopropylethylamine, in an inert solvent (such as methylene chloride), preferably at room temperature.

The starting materials of formula II, such as optionally substituted phenylureidophenylacetic acids, are in turn known in the art or are prepared according to methods known in the art, e.g. by, for example, condensing a p-aminophenylacetic acid ester with the appropriate aryl isocyanate to obtain the corresponding phenylureidophenylacetic acid ester and hydrolyzing the resulting ester.

The starting materials of formula III are in turn prepared by reacting a compound of the formula IV

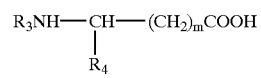

wherein the carboxyl group is in protected form (e.g. as an alkyl ester) and $R_3$, $R_4$ and m have meaning as defined hereinabove, with a compound of the formula V

preferably as a reactive functional derivative thereof, wherein Z is $(CH_2)_{n'}$ or $CHR_6$, and n, n' and $R_6$ have meaning as defined hereinabove and L is a leaving group, such as halo or (alkyl or aryl)-sulfonyloxy, in the presence of a base, such as triethylamine, to obtain a compound of the formula VI

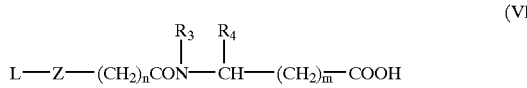
(VI)

wherein the carboxylic acid is in protected form (e.g. as an alkyl ester), and L, $R_1$, $R_2$ and Z have meaning as defined hereinabove, which is in turn reacted with an amine of the formula IX

(VII)

wherein $R_2$ has meaning as defined hereinabove under conditions well-known in the art, to obtain a starting material of formula III in protected form (e.g. as an alkyl ester). Hydrolysis, e.g. with base, such as aqueous lithium hydroxide, gives a starting material of formula III.

As noted above in the cited processes, such may be carried out while, if necessary, temporarily protecting any interfering reactive group(s), and then liberating the resulting compound of the invention. In starting compounds and intermediates which are converted to the compounds of the invention in a manner described herein, functional groups present, such as carboxyl, amino and hydroxy groups, are optionally protected by conventional protecting groups that are a common in preparative organic chemistry. Well-known protecting groups and their introduction are described, for example, in J. F. W. McOmie, "Protective Groups in Organic Chemistry", Plenum Press, London, New York, T. W. Greene, "Protective Groups in Organic Synthesis", Wiley, New York. For example, a hydroxy group is advantageously protected in the form of a benzyl ether which can be cleaved by catalytic hydrogenation to obtain a hydroxy substituted product.

The resulting compounds of formula I wherein X is esterified carboxyl ($COOR_5$) can be converted to the corresponding acids e.g. by hydrolysis according to methods well-known in the art.

The abbreviations used in the following Examples have the indicated meaning:

conc.=concentrated
DEIA=di-isopropylethylamine
DMSO=dimethyl sulfoxide
EDAC=1-[3-(dimethylamino)propyl]-3-ethylcarbodiimide hydrochloride
HOBT=hydroxybenzotriazole
HOSu=hydroxysuccinamide
HPLC=high pressure liquid chromatography
MS=mass spectroscopy
NMR=nuclear magnetic resonance
OR=optical rotation
TEA=triethylamine
TLC=thin layer chromatography
TRIS=tris(hydroxymethyl)aminomethane

EXAMPLE 1

(S)-β-[3-methoxypropyl)[[4-[(2-methylphenylaminocarbonylamino)phenyl]acetyl]amino]acetylamino-benzenepropanoic acid Step 1

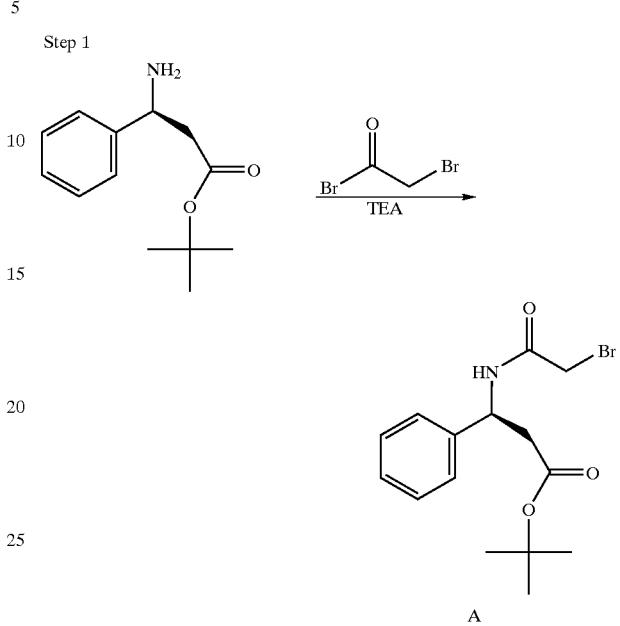

To 45 mL $CH_2Cl_2$ 1 g (4.5 mmol) 1,1-dimethyl ethyl (3S)-3-amino-3-phenyl -phenylpropanoate is added. Then 0.720 mL (5.17 mmol) TEA is added. The mixture is stirred 10 min., and cooled 0° C. To the mixture is added 0.450 mL (5.17 mmol) bromoacetyl bromide in 5 mL $CH_2Cl_2$ dropwise over 15 min. The mixture is stirred over 3 hrs., allowing it to reach room temp. TLC, using 50% ethyl acetate/50% hexanes, is used to monitor the reaction. The mixture is reduced to dryness and flash chromatographed using 30 g silica gel, Merck, grade 9385, 230–400 mesh, 60 A, using 25% ethyl acetate/75% hexanes, to yield 1.75 g thick yellow oil, which shows one spot on TLC. The product is carried on to next step.

Step 2

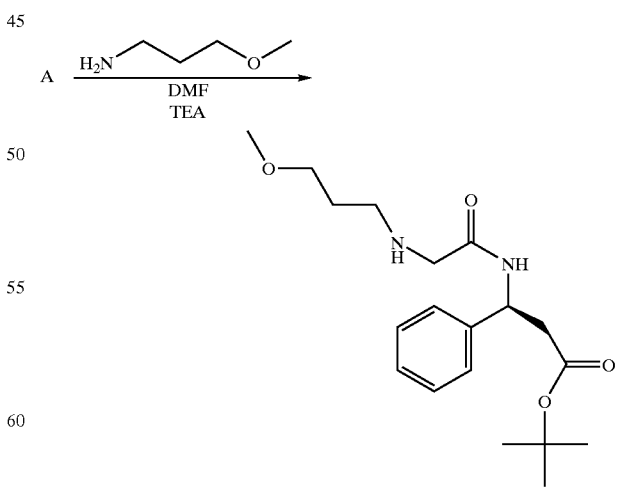

To 50 mL DMF is added 1.5 g A and 1.0 g (11 mmol) 3-methoxy-propylamine. At room temp. 0.74 mL (5.3 mmol) triethylamine is added. The mixture is stirred 16 hrs. at room. temp. TLC, using 10% CH$_3$OH/90% CH$_2$Cl$_2$, is used to monitor the reaction. The mixture is reduced to dryness and flash chromatographed using 45 g silica gel, starting with 2% and gradually increasing to 4% CH$_3$OH/CH$_2$Cl$_2$, to yield 1.6 g yellow oil, which shows one spot on TLC. The product is carried on to the next step.

Step 3

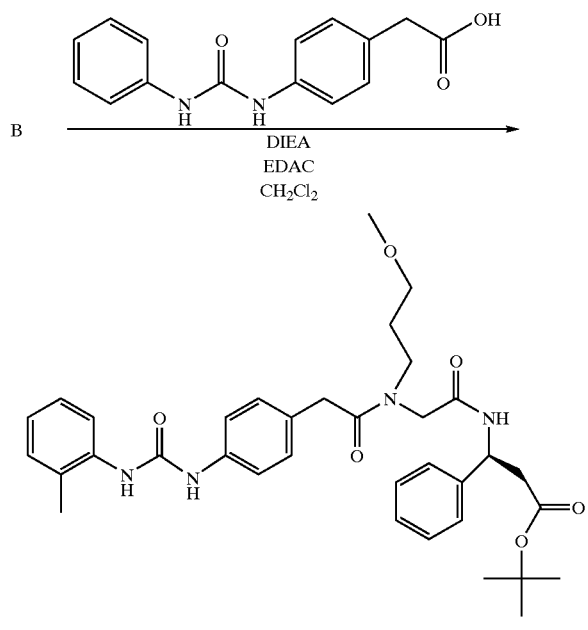

To 50 mL CH$_2$Cl$_2$ is added 1.5 g B. Then 1.4 g (4.8 mmol) N-(2-methyl)-N'-(4'-acetic acid)diphenyl urea (only partially soluble) and 0.74 mL (5.3 mmol) DIEA is added. The mixture is stirred 15 min. at room temp. to give a clear yellow solution. 0.98 g (4.8 mmol) EDAC is added and the mixture stirred 3 hrs. TLC, using 10% CH$_3$OH/90% CH$_2$Cl$_2$, is used to monitor the reaction. The mixture is reduced to dryness and flash chromatographed using 90 g silica gel, starting with 1% and increasing to 5% CH$_3$OH/CH$_2$Cl$_2$, to yield 1.93 g white foam.

Step 4

C    20% TFA/CH$_2$Cl$_2$

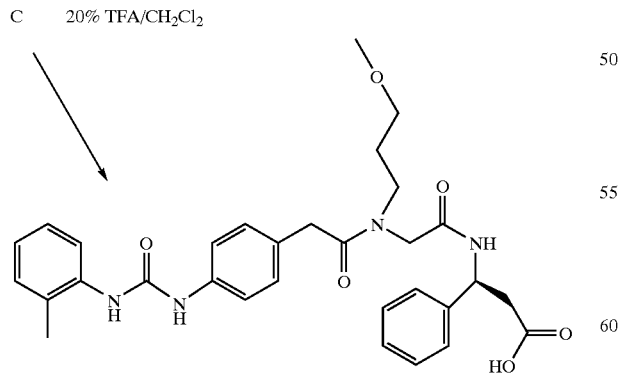

To 35 ml CH$_2$Cl$_2$ at room temp is added 1.7 g C. Then 8 mL TFA acid is added dropwise with 5 mL CH$_2$Cl$_2$. The mixture is stirred 2 hrs. TLC, using 10% CH$_3$OH/90% CH$_2$CL$_2$, is used to monitor the reaction. The mixture is reduced to dryness. Fresh CH$_2$Cl$_2$ is added several times to remove all TFA. The product is flash chromatographed using 50 g silica gel and 2% to 5% CH$_3$OH/CH$_2$C;$_2$ to yield 1.5 g of the title compound as a white powder.

mp: 125–127° C.

OR: −27.4°, DMSO (10 mg/mL)

EXAMPLE 2

(S)-[3-methoxypropyl)[[4-[(2-methylphenylaminocarbonylamino)phenyl]acetyl]amino]acetylamino-4-hexanoic acid Step 1

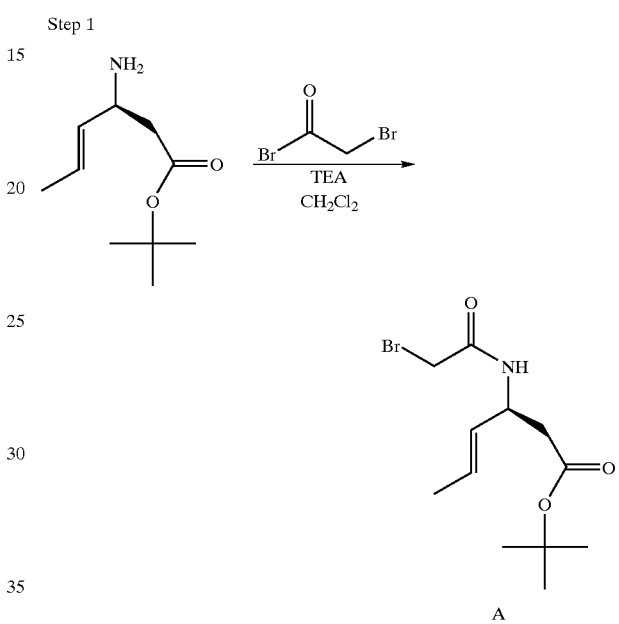

Following the procedure of Example 1, step 1, but starting with 0.834 g (4.5 mmol) 1,1-dimethylethyl(3S)-3-amino-4-hexeneoate there is obtained 01.46 g thick yellow oil, which shows one spot on TLC. The product is carried on to the next step.

Step 2

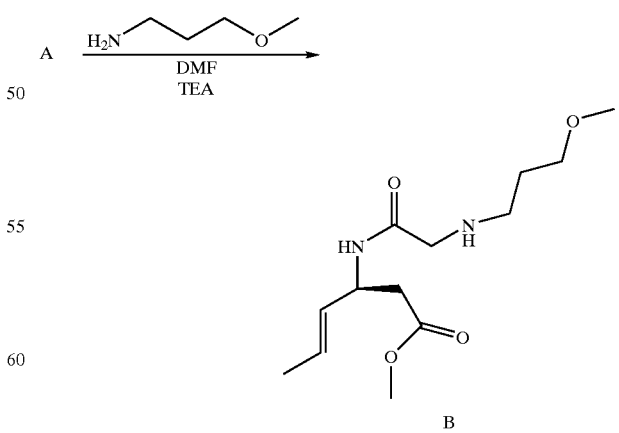

To 10 mL DMF is added 0.31 g (1 mmol) A. Then 0.18 g (2 mmol) 3-methoxypropylamine is added. At room temp. 0.23 mL (2 mmol) TEA is added. The mixture is stirred 16 hrs. at room. temp. TLC, using 10% CH₃OH/90% CH₂Cl₂, is used to monitor the reaction. The mixture is reduced to dryness and flash chromatographed using 12 g silica gel, starting with 2% and gradually increasing to 4% CH₃OH/CH₂Cl₂, to yield 0.1 g yellow oil, which shows one spot on TLC. The product is carried on to the next step.

Step 3

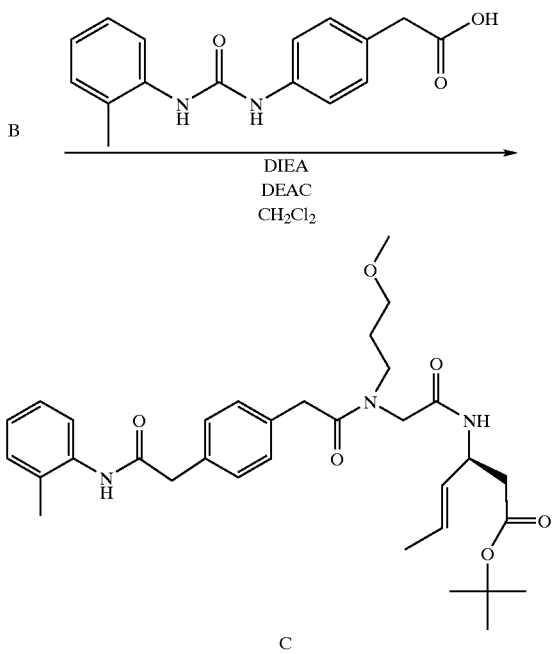

To 50 mL CH₂Cl₂ is added 1.4 g (4.4 mmol) B. Then 1.4 g (4.8 mmol) N-(2-methyl)-N'-(4'-acetic acid) diphenyl urea, only partially soluble, and 0.74 mL (5.3 mmol) DIEA are added and the mixture stirred 15 min. to give a clear yellow solution. 0.98 g (4.8 mmol) EDAC is added and the mixture stirred 3 hrs. TLC, using 10% CH₃OH in CH₂Cl₂, is used to monitor the reaction. The mixture is reduced to dryness, flashed chromatographed using 90 g silica gel, starting with 1% and increasing to 5% CH₃OH in CH₂Cl₂, to yield 1.8 g white foam.

Step 4

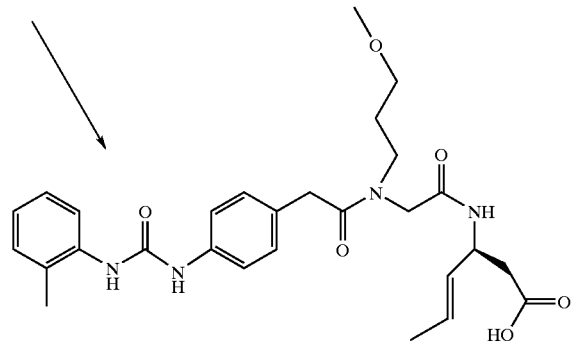

To 35 ml CH₂Cl₂ at room temp is added 1.7 g C. Then 8 mL TFA is added dropwise with 5 mL CH₂Cl₂. The mixture is stirred 2 hrs. TLC, using 10% CH₃OH/90% CH₂CL₂, is used to monitor the reaction. The mixture is reduced to dryness. Fresh CH₂Cl₂ is added several times to remove all TFA. The product is flash chromatographed using 50 g silica gel and 2% to 5% CH₃OH/CH₂Cl₂ to yield 1.5 g of the title compound as a white powder.

mp: 88–90° C.

EXAMPLE 3

(S)-β-[3-methoxypropyl)[[4-[(2-methylphenylaminocarbonylamino)phenyl]acetyl]amino]acetylamino-3,4-dimethoxy-benzenepropanoic acid Step 1

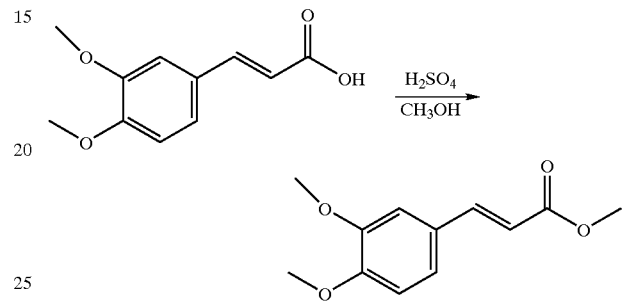

To 300 mL CH₃OH is 30 g (144.2 mmol) 3,4-dimethoxycinnamic acid. Four drops H₂SO₄ is added and the mixture refluxed for 4 hrs. TLC, using 70/30, ethyl acetate/ hexanes, is used to monitor the reaction. The mixture is reduced to dryness and flash chromatographed, using 20% ethyl acetate 80% hexanes, on 350 g silica gel, grade 60, 70–230 mesh, to yield 14.14 g A.

Step 2

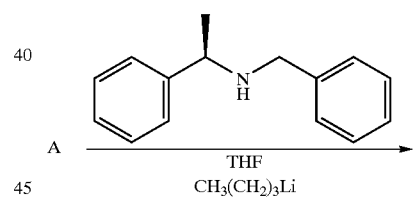

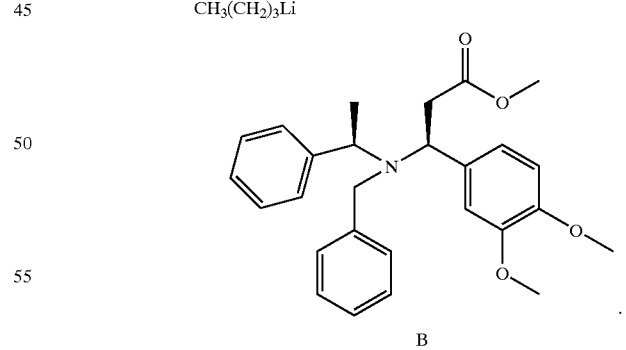

To 200 mL THF is added 11.8 g (55.8 mmol) (R)-(+)-N-benzyl α-methylbenzylamine. The mixture is cooled to 0° C. and 34.9 mL (55.8 mmol) n-buLi (1.6 M in hexanes) added dropwise over 30 min. The mixture is stirred for an 30 additional min. The reaction is cooled to −78° C. Then 6.2 g (27.9 mmol) methyl 3,4-dimethoxycinnamate, dissolved in 150 mL THF, is added dropwise over 1 hr. The mixture is stirred for 30 min. at −78° C. and slowly, maintaining −78°

C., 25 mL saturated NH$_4$Cl solution is added and the mixture warmed to room temp., washed with brine, and reduced to dryness. TLC, using 50/50, ethyl acetate/hexanes, is used to monitor the reaction. The mixture is flashed chromatographed on 180 g silica gel, Merck, grade 9385, 230–400 mesh, 60 A, to yield 10.5 g thick yellow oil.

Step 3

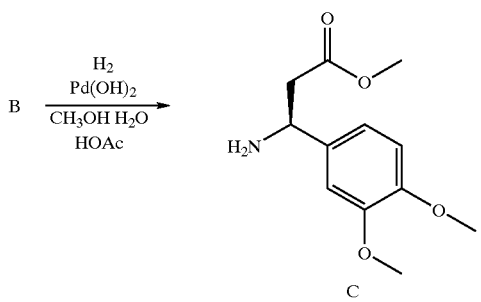

5.0 g (11.5 mmol) B is added to 250 mL CH$_3$OH, 25 mL H$_2$O, and 7.5 mL HOAc. 1 g Pearlman's catalyst (Pd (OH)$_2$) is added. Using a ballon, the mixture is refluxed in an H$_2$ atmosphere for 16 hrs. at room temp. TLC, using 5% CH$_3$OH/CH$_2$Cl$_2$, is used to monitor the reaction. The mixture is filtered through celite, washed with CH$_3$OH, and reduced to dryness. To the dry product is added CH$_2$Cl$_2$ and it is washed with brine made basic with sat'd NaHCO$_3$. The mixture is reduced to dryness and flash chromatographed using 150 g silica gel, 230–400 mesh, 1 to 4% CH$_3$OH/CH$_2$Cl$_2$, to yield 1.54 g yellow oil.

Step 4

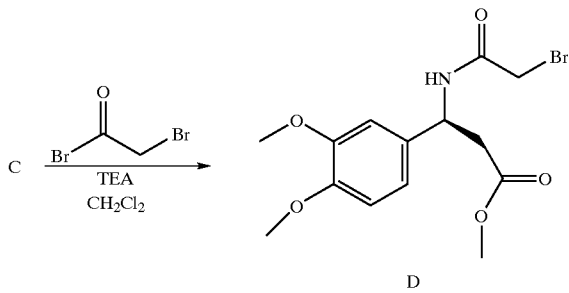

To 9 mL CH$_2$Cl$_2$ is added 0.2 g (0.8 mmol) C and 0.13 mL (0.9 mmol) TEA. The mixture is stirred 10 min. and the mixture cooled to 0° C. 0.08 mL (0.9 mmol) bromoacetyl bromide in 1 mL CH$_2$Cl$_2$ is added dropwise over 15 min. The mixture is stirred over 3 hrs. allowing the mixture to reach room temp. TLC, using 50% ethyl acetate/50% hexanes, is used to monitor the reaction. The mixture is reduced to dryness and flash chromatographed using 30 g silica gel, Merck, grade 9385, 230–400 mesh, 60 A, using 25% ethyl acetate/75% hexanes, to yield 0.237 g thick yellow oil, which shows one spot on TLC. The product is carried on to next step.

Step 5

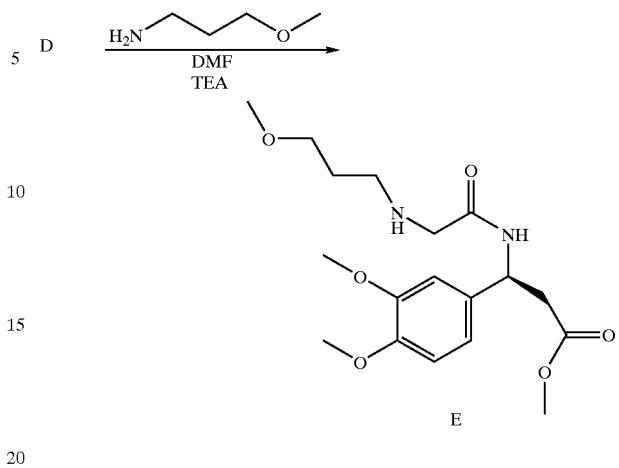

To 10 mL DMF are added 0.36 g (1 mmol) D and 0.18 g (2 mmol) 3-methoxypropylamine. At room temp. 0.23 mL TEA is added. The mixture is stirred 16 hrs. at room. temp. TLC, using 10% CH$_3$OH/90% CH$_2$Cl$_2$, is used to monitor the reaction. The mixture is reduced to dryness and flash chromatographed using 12 g silica gel, starting with 2% and gradually increasing to 4% CH$_3$OH/CH$_2$Cl$_2$, to yield 0.1 g yellow oil, which shows one spot on TLC. The product is carried on to the next step.

Step 6

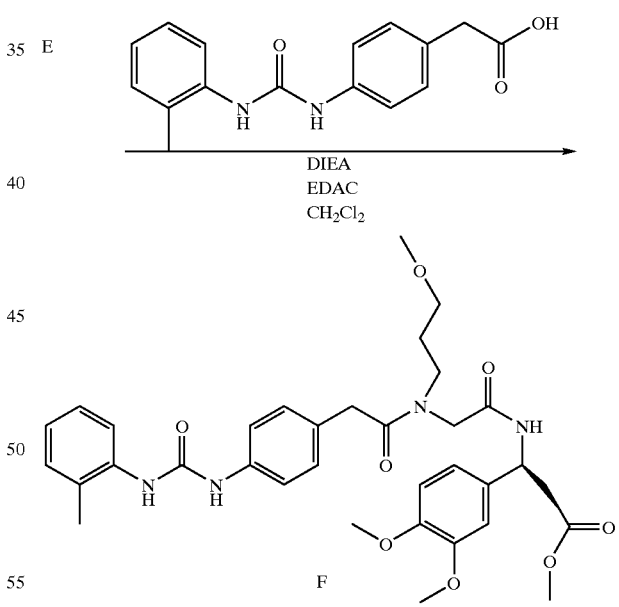

To 5 mL CH$_2$Cl$_2$ is added 0.1 g (0.27 mmol) E and 0.0853 g (0.30 mmol) N-(2-methyl)-N'-(4'-acetic acid) diphenyl urea, which is only partially soluble. 0.056 mL (0.34 mmol) DIEA is added and the mixture stirred 15 min. at room temp. to give a clear yellow solution. 0.058 g (0.30 mmol) EDAC is added and the mixture stirred 3 hrs. TLC, using 10% CH$_3$OH/90% CH$_2$Cl$_2$, is used to monitor the reaction. The mixture is reduced to dryness, flash chromatographed using 90 g silica gel, using 1% increasing to 5% CH$_3$OH/CH$_2$Cl$_2$, to yield 0.113 g white foam.

Step 7

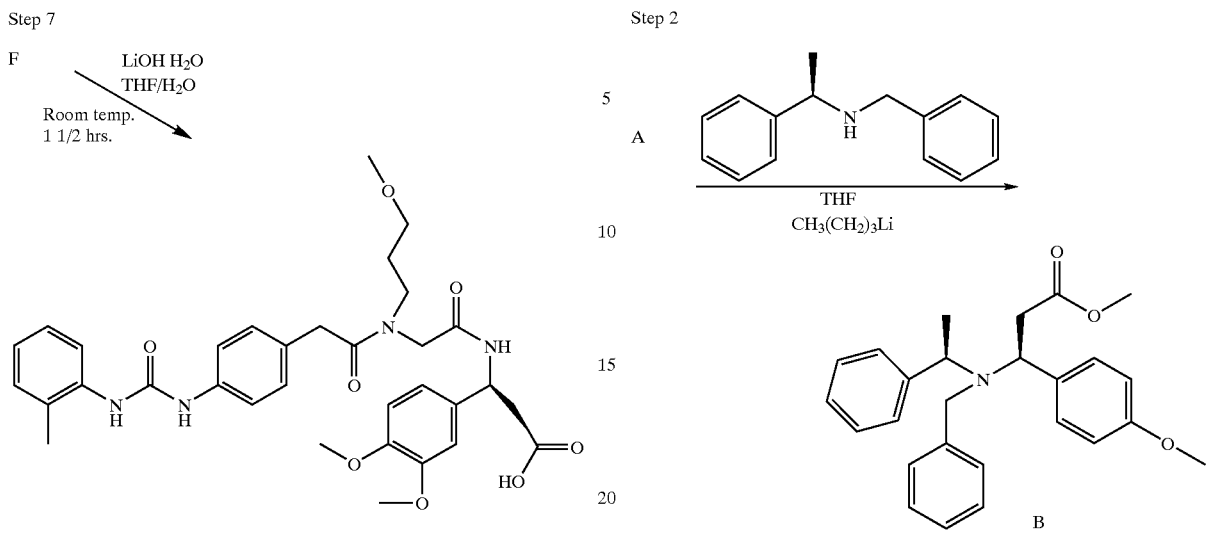

To 21 mL THF and 8 mL H₂O is added 0.36 g (0.57 mmol) F. 0.36 g (0.86 mmol) LiOH dissolved in 1 mL H₂O is added dropwise over 5 min. and the mixture stirred for two hrs. at room temp. TLC, using 10% CH₃OH/CH₂Cl₂, is used to monitor the reaction. The mixture is reduced to dryness and flash chromatographed on 20 g silica gel, using 100% CH₂Cl₂ to 5% CH₃OH/CH₂Cl₂, to yield 0.36 g of the title compound as a white powder.

mp: 118–120° C.

OR:=−33.6°, DMSO (10 mg/ mL)

EXAMPLE 4

(S)-β-[3-methoxypropyl)[[4-[(2-methylphenylaminocarbonylamino)phenyl]acetyl]amino]acetylamino--4- methoxy-benzene propanoic acid, sodium salt acid

Step 1

To 250 mL CH₃OH is added 50 g (280.8 mmol) 4-dimethoxycinnamic acid and 2 mL conc. H₂SO₄. The mixture is refluxed for 6 hrs. TLC using 70/30, ethyl acetate/hexanes, is used to monitor the reaction. About 30 mL CH₃OH is removed. The mixture is cooled to r.t, and then crystalized, filtered, washed with H₂O, and dried to yield 49.23 g of the desired product.

Step 2

To 300 mL THF is added 10.99 g (52 mmol) (R)-(+)-N-benzyl-α-methylbenzylamine. The mixture is cooled to 0° C. and 32.5 mL (52 mmol) n-buLi (1.6 M in hexanes) added dropwise over 30 min. The mixture is stirred for an 30 additional min. The reaction is cooled to −78° C. Then 5 g (26 mmol) methyl 4-methoxycinnamate, dissolved in 100 mL THF, is added dropwise over 1 hr. The mixture is stirred for 30 min. at −78° C. and slowly, maintaining −78° C., 25 mL saturated NH₄Cl solution is added and the mixture warmed to room temp., washed with brine, and reduced to dryness. TLC, using 50/50, ethyl acetate/ hexanes, is used to monitor the reaction. The mixture is flashed chromatographed on 180 g silica gel, Merck, grade 9385, 230–400 mesh, 60 Å to yield 9.738 g thick pale-yellow oil (recrystalized from EtOAc/hexanes to give white crystals).

Step 3

7.74 g (19.2 mmol) B is added to 250 mL CH₃OH, 25 mL H₂O, and 7.5 mL HOAc. 1 g Pearlman's catalyst is added. Using a hydrgen ballon, the mixture is refluxed in an H₂ atmosphere for 16 hrs. at room temp. TLC, using 5% CH₃OH/CH₂Cl₂, is used to monitor the reaction. The mixture is filtered through celite, washed with CH₃OH, and reduced to dryness. To the dry product added CH₂Cl₂ and it is washed with brine made basic with sat'd NaHCO₃. The mixture is reduced to dryness and flash chromatographed using 150 g silica gel, used 230–400 mesh, using 1 to 4% CH₃OH/CH₂Cl₂, to yield 3.4 g thick pale-yellow oil (recrystalized from EtOAc/hexanes to give white crystals).

Step 4

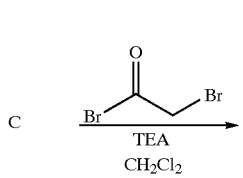 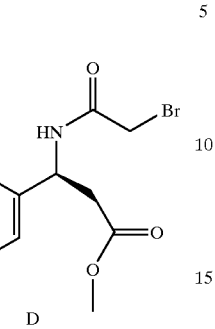

To 25 mL CH₂Cl₂, is added 0.8 g (3.82 mmol) C and 0.62 mL (4.4 mmol) TEA. The mixture is stirred 10 min. and the mixture cooled to 0° C. 0.38 mL (4.4 mmol) bromoacetyl bromide in 5 mL CH₂Cl₂ is added dropwise over 15 min. The mixture is stirred over 3 hrs. allowing the mixture to reach room temp. TLC, using 50% ethyl acetate/50% hexanes, is used to monitor the reaction. The mixture is reduced to dryness and flash chromatographed using 30 g silica gel, Merck, grade 9385, 230–400 mesh, 60 Å, using 25% ethyl acetate/75% hexanes, to yield 0.1.3 g thick yellow oil, which shows one spot on TLC. The product is carried on to next step.

Step 5

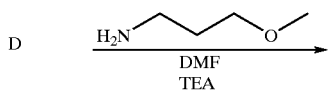

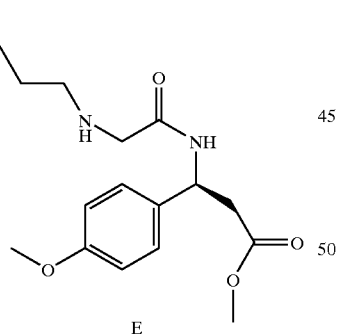

To 70 mL DMF are added 1.3 g (3.94 mmol) D and 0.667 g (7.49 mmol) 3-methoxypropylamine. At room temp. 0.1.05 mL (7.49 mmol) TEA is added. The mixture is stirred 16 hrs. at room. temp. TLC, using 10% CH₃OH/90% CH₂Cl₂, is used to monitor the reaction. The mixture is reduced to dryness and flash chromatographed using 75 g silica gel, starting with 2% and gradually increasing to 4% CH₃OH/CH₂Cl₂, to yield 1.29 g yellow oil which shows one spot on TLC. The product is carried on to the next step.

Step 6

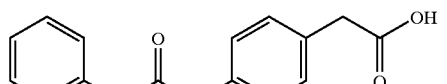

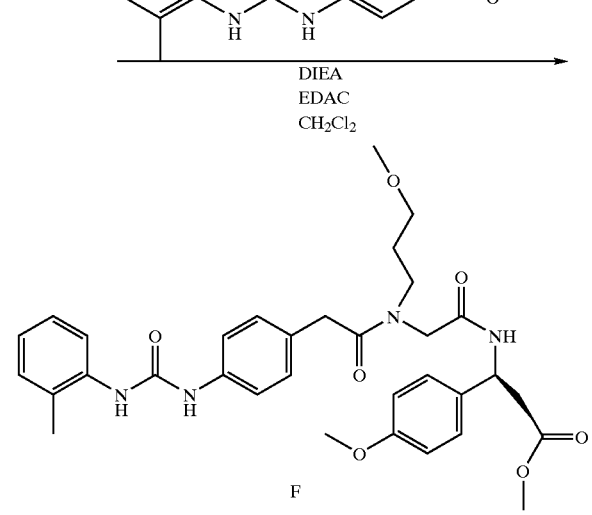

To 30 mL CH₂Cl₂ are added 0.72 g (2.1 mmol) E and 0.739 g (2.6 mmol) N-(2-methyl)-N'-(4'-acetic acid) diphenyl urea, which is only partially soluble. 0.46 mL (2.6 mmol) DIEA is added and the mixture stirred 15 min. at room temp. to give a clear yellow solution. 0.499 g (2.6 mmol) EDAC is added and the mixture stirred 3 hrs. TLC, using 10% CH₃OH/90% CH₂Cl₂, is used to monitor the reaction. The mixture is reduced to dryness, flash chromatographed using 90 g silica gel, using 1% increasing to 5% CH₃OH/CH₂Cl₂, to yield 0.920 g white foam.

Step 7

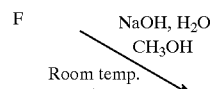

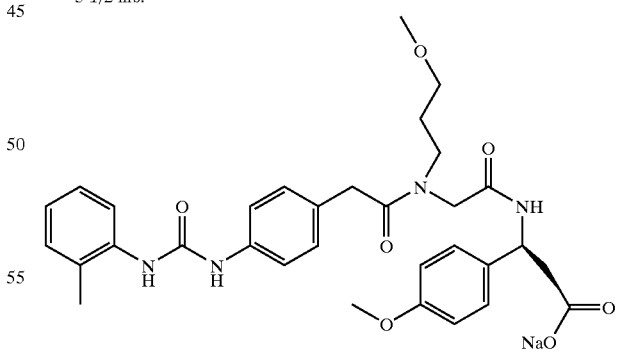

To 30 mL EtOH and 8 mL H₂O is added 0.90 g (1.49 mmol) F. To the mixture is added 0.057 g (1.42 mmol) NaOH in 1 mL H₂O. The mixture is stirred 3.5 hrs. at r.t. The mixture is filtered and dried to yield 0.720 g of the title compound as a white solid.

mp: 216–118° C. (dec)

OR: −21.069° in DMSO (5.3 mg/mL)

EXAMPLE 5

Prepared similarly to the previous examples are the compounds of the formula

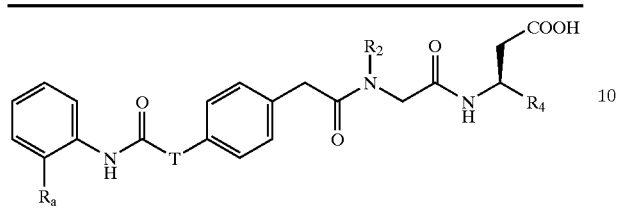

| Compound | $R_a$ | T | $R_2$ | $R_4$ | m.p. (° C.) |
|---|---|---|---|---|---|
| (a) | $CH_3$ | NH | $(CH_2)_4OCH_3$ | 3,4-dimethoxyphenyl | 114–117 (dec) |
| (b) | $CH_3$ | NH | $(CH_2)_4OCH_3$ | Phenyl | 116–118 (dec) |
| (c) | $CH_3$ | $CH_2$ | $(CH_2)_3OCH_3$ | 4-methoxyphenyl | 127–130 (dec) |
| (d) | H | NH | $(CH_2)_3OCH_3$ | Phenyl | 107–111 (dec) |
| (e) | Cl | NH | $(CH_2)_3OCH_3$ | Phenyl | 118–122 |
| (f) | $NH_2$ | NH | $(CH_2)_3OCH_3$ | Phenyl | 105–109 (dec) |

What is claimed is:

1. A compound of the formula I

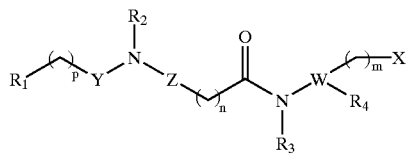

wherein $R_1$ is N-arylureido-substituted phenyl; $R_3$ is H, alkyl, alkenyl, aryl or heteroaryl; $R_4$ is alkenyl, carbocyclic aryl or heteroaryl; $R_2$ and $R_6$, together with the carbons to which they are attached, form a heterocycle selected from piperidine, morpholine, pyrrolidine, thiazolidine and piperazine; Z is $CHR_6$; m is 1–4; n is 0–4; p is 1–4; W is CH; Y is CO; X is $CO_2H$ or $CO_2$alkyl; or a pharmaceutically acceptable salt thereof.

2. A compound according to claim 1 of formula Ie

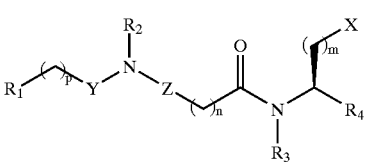

wherein $R_1$, $R_2$, $R_3$, $R_4$, X, Y, Z, m, n and p are as defined in claim 1, or a pharmaceutically acceptable salt thereof.

3. A composition comprising a compound of claim 1 together with a pharmaceutically acceptable carrier.

4. A method of inhibiting VLA-4 (very late antigen4), dependent cell adhesion in a mammal which comprises administering to a mammal in need thereof an effective cell adhesion inhibiting amount of a compound of claim 1 for a time and under conditions effective to inhibit VLA4-dependent cell adhesion.

* * * * *